United States Patent [19]

Dubief

[11] Patent Number: 5,690,920
[45] Date of Patent: Nov. 25, 1997

[54] FOAMABLE WASHING COMPOSITION BASED ON SELECTED INSOLUBLE SILICONES AND AN ALKYLPOLYGLYCOSIDE, AND COSMETIC AND DERMATOLOGICAL USES THEREOF

[75] Inventor: Claude Dubief, Le Chesnay, France

[73] Assignee: L'Oreal, Paris, France

[21] Appl. No.: 487,478

[22] Filed: Jun. 7, 1995

Related U.S. Application Data

[63] Continuation of Ser. No. 64,015, filed as PCT/FR91/00900, Nov. 15, 1991 published as WO92/08439, May 29, 1992, abandoned.

[30] Foreign Application Priority Data

Nov. 15, 1990 [FR] France .................. 90 14223

[51] Int. Cl.$^6$ ............................................. A61K 7/06
[52] U.S. Cl. ........................... 424/70.12; 424/70.31; 510/122; 510/130
[58] Field of Search ............. 424/70.12, 70.121, 424/70.21, 70.31; 252/174.15, DIG. 5, DIG. 13, DIG. 2; 510/119, 122, 130, 158, 159

[56] References Cited

U.S. PATENT DOCUMENTS

| | | | |
|---|---|---|---|
| 4,563,347 | 1/1986 | Starch | 424/70 |
| 4,601,902 | 7/1986 | Fridd et al. | 424/70 |
| 4,957,732 | 9/1990 | Grollier et al. | 424/73 |
| 4,973,476 | 11/1990 | Krzysik | 424/71 |
| 4,978,561 | 12/1990 | Cray et al. | 427/387 |
| 5,035,832 | 7/1991 | Takamura et al. | 252/174.15 |
| 5,057,311 | 10/1991 | Kamegai et al. | 424/70 |
| 5,063,044 | 11/1991 | Kohl et al. | 424/70 |
| 5,063,051 | 11/1991 | Grollier et al. | 424/70.12 |
| 5,063,052 | 11/1991 | Grollier et al. | 424/70 |
| 5,104,555 | 4/1992 | Foster et al. | 510/327 |
| 5,133,897 | 7/1992 | Balzer | 252/312 |
| 5,160,730 | 11/1992 | Dubief et al. | 424/59 |
| 5,268,126 | 12/1993 | Balzer | 252/312 |
| 5,275,755 | 1/1994 | Sebag et al. | 252/174.15 |
| 5,409,628 | 4/1995 | Heinz et al. | 252/174.17 |
| 5,409,640 | 4/1995 | Giret et al. | 252/546 |

FOREIGN PATENT DOCUMENTS

| | | |
|---|---|---|
| 0 194 097 | 9/1986 | European Pat. Off. . |
| 0 337 354 | 10/1989 | European Pat. Off. . |
| 0 398 177 | 11/1990 | European Pat. Off. . |
| 0 418 479 | 3/1991 | European Pat. Off. . |
| 2 128 627 | 5/1984 | United Kingdom . |

*Primary Examiner*—John C. Bleutge
*Assistant Examiner*—Robert H. Harrison
*Attorney, Agent, or Firm*—Jacobson, Price, Holman & Stern, PLLC

[57] ABSTRACT

A foamable washing composition for hair and skin care contains: an insoluble silicone selected from silicone gums, silicone resins, and organomodified silicones comprising one or more thiol, carboxylate, γ-hydroxypropyl, alkylcarboxylic acid, hydroxyalkylsulphonate, hydroxyalkylthiosulphate or hydroxyacylamino groups, and mixtures thereof; and 4–60% by weight of a compound of formula (I) which corresponds to structure (II), where R denotes a $C_8$–$C_{24}$ alkyl or alkenyl radical or radical mixture, and x is 1–15; the weight ratio of the compound of formula (I) and the silicone being equal to or greater than 1.

18 Claims, No Drawings

FOAMABLE WASHING COMPOSITION BASED ON SELECTED INSOLUBLE SILICONES AND AN ALKYLPOLYGLYCOSIDE, AND COSMETIC AND DERMATOLOGICAL USES THEREOF

This is a continuation of application Ser. No. 08/064,015, filed as PCT/FR91/00900, Nov. 15, 1991 published as WO92/08439, May 29, 1992, abandoned.

The invention relates to foamable washing compositions based on selected insoluble silicones and an alkylpolyglycoside, and cosmetic and dermatological uses thereof.

Silicone oils are already used in cosmetics as lubricants in hair or skin treatment compositions or as "anti-foam" agents in nonrinsed lotions. The majority of them are insoluble in water.

Shampoos based on water-insoluble silicones and a surface-active agent are also known, the silicones being dispersed in the medium by fatty acid alkanol-amides, ethylene glycol stearates or dimethyl ($C_{16}$–$C_{22}$) alkylamines N-oxides.

The Applicant has surprisingly discovered that it was possible to obtain a foamable washing composition based on selected water-insoluble silicones by using an alkylpolyglycoside as dispersing agent and detergent.

The subject of the invention is thus novel foamable washing compositions based on water-insoluble silicones defined below and on at least one cosmetically acceptable alkylpolyglycoside.

Another subject of the invention is a hair washing and conditioning process and a skin washing process using these compositions.

Other subjects will become apparent on reading the description and examples which follow.

The present invention mainly relates to a foamable washing composition, characterized in that it contains, in an aqueous medium:

a) a silicone which is insoluble in the said medium and unreactive with the latter, chosen from silicone gums, silicone resins or organomodified silicones containing one or a number of thiol, carboxylate, γ-hydroxypropyl, alkylcarboxylic acid, hydroxyalkylsulfonate, hydroxyalkylthiosulfate or hydroxyacylamino groups, and mixtures thereof;

b) from 4 to 60% of at least one compound corresponding to the following formula:

or also corresponding to the expanded structure (II):

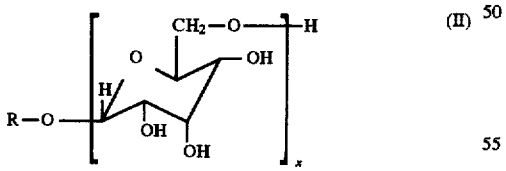

in which:

R denotes a straight- or branched-chain, $C_8$–$C_{24}$ alkyl or alkenyl radical or a mixture of straight- or branched-chain, $C_8$–$C_{24}$ alkyl or alkenyl radicals;

x is a number from 1 to 15;

the compound of formula (I)/insoluble silicone ratio by weight being greater than or equal to 1.

The silicones, used in accordance with the present invention, are polyorganosiloxanes insoluble in aqueous media, which can exist in the form of oils, waxes, gums or resins., The organopolysiloxanes are defined in more detail in the work by Walter Noll, "Chemistry and Technology of Silicones" (1968), Academic Press.

These silicones must not be reactive with said media.

The polysiloxanes used, in accordance with the invention, are chosen from silicone gums and resins, organomodified polysiloxanes defined below and mixtures thereof.

Silicone gums, in accordance with the present invention, are polydiorganosiloxanes having high molecular masses of between 200,000 and 1,000,000.

There are mentioned, for example, the following gums:

poly(dimethylsiloxane/methylvinylsiloxane), poly(dimethylsiloxane/diphenylsiloxane), poly(dimethylsiloxane/phenylmethylsiloxane), poly(dimethylsiloxane/diphenylsiloxane/methylvinylsiloxane).

Organopolysiloxane resins which can be used in accordance with the invention are crosslinked siloxane systems containing $R'_2SiO_{2/2}$, $R'SiO_{3/2}$ and $SiO_{4/2}$ units in which R' represents a hydrocarbon group having 1 to 6 carbon atoms or a phenyl group. Among these products, those particularly preferred are those in which R' denotes a lower alkyl radical or a phenyl radical.

Among these resins, there may be mentioned the product sold under the name Dow Corning 593, which is a mixture of trimethylsiloxysilicate and of polydimethylsiloxane, or those sold under the names SILICONE FLUID SS 4230 and SS 4267 by the Company General Electric and which are "dimethyl/trimethylpolysiloxanes".

Organomodified silicones are polyalkylsiloxanes, polyarylsiloxanes or polyalkylarylsiloxanes containing, in their structure, one or a number of organofunctional groups connected directly to the siloxane chain or connected via a hydrocarbon radical.

Among these silicones, there may be mentioned, for example, the silicones containing:

1—thiol groups as in GP 72 A and GP 71 of Genesee or in the product SLM 50253/5 of the Company Wacker, 2—carboxylate groups as in the products described in Patent EP-A-186,507 of the Company Chisso Corporation, 3—γ-hydroxypropyl groups, such as the products described in French Patent Application No. FR-85/16/334, corresponding to the following formula (III):

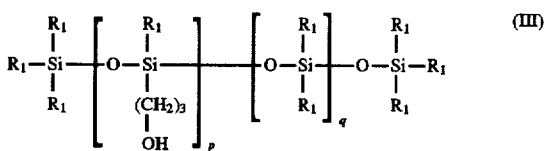

in which:

the radicals $R_1$, which are identical or different, are chosen from methyl and phenyl radicals, at least 60 mol % of the radicals $R_1$ denoting methyl;

p is between 1 and 30 inclusive;

q is between 1 and 150 inclusive.

There is mentioned, for example, the product 71615 V 300 sold by the Company Rhône-Poulenc.

4—Acyloxyalkyl groups, such as, for example, the polyorganosiloxanes described in U.S. Pat. No. 4,957,732, corresponding to the formula:

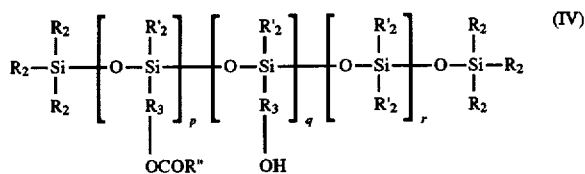

in which:

R₂ denotes a methyl, phenyl, —OCOR" or hydroxyl group, only one of the radicals R₂ per silicon atom may be OH;

R'₂ denotes methyl or phenyl, at least 60 mol % of the radicals R₂ and R'₂ combined denoting methyl;

R" denotes a $C_8$-$C_{20}$ alkyl or alkenyl;

R₃ denotes a linear or branched, divalent $C_2$-$C_{18}$ alkylene hydrocarbon radical;

r is between 1 and 120 inclusive;

p is between 1 and 30;

q is equal to 0 or is less than 0.5 p, p+q being between 1 and 30; it being possible for the polyorganosiloxanes of formula (IV) to contain

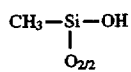

in proportions not exceeding 15% of the sum p+q+r.

5—carboxyl-type anionic groups such as alkylcarboxyl groups such as those present in the product X-22-3701E of the Company Shin-Etsu or in the product SILICONE FLUID FZ 3703 of the Company Union Carbide; 2-hydroxyalkylsulfonate; 2-hydroxyalkylthiosulfate such as the product sold by the Company Goldschmidt under the names ABIL S201 and ABIL S255.

6—silicones containing hydroxyacylamino functional groups chosen especially from the compounds of formula:

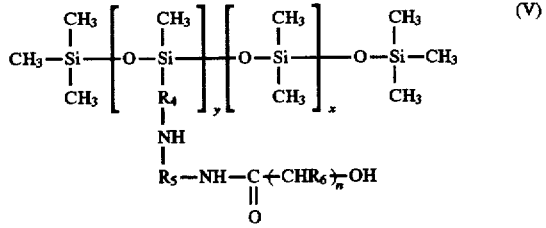

in which:

R₄ and R₅ denote (CH₂)₂, (CH₂)₃, (CH₂)₄ or —CH₂CH(CH₃)CH₂—;

R₅ denotes hydrogen, hydroxyl, alkyl or hydroxyalkyl;

n is an integer varying from 2 to 7;

x is an integer varying from 20 to approximately 1500;

y varies between approximately 0.5 and 10;

and the ratio y/x is less than 0.05.

Such silicones are more particularly described in European Patent Application EP-A-0,342,834.

A more particularly preferred silicone is that corresponding to the formula (V), in which:

R₄ denotes —CH₂CH(CH₃)CH₂—;
R₅ denotes —(CH₂)₂—;
R₆ denotes hydrogen;
x is equal to 392;
y is equal to 8;
n is equal to 3.

Such silicones are sold in particular under the name Q2-8413 by the Company Dow Corning.

The more particularly preferred polyorganosiloxanes, in accordance with the invention, are silicone gums and organomodified silicones of paragraphs 1, 2 and 5 defined above.

Water-insoluble silicones, which can be used in accordance with the present invention and as defined above, are present in the compositions in proportions of between 0.2 and 30% and preferably of between 0.4 and 15% with respect to the total weight of the compositions.

The alkylpolyglycoside compounds of expanded formula (II) defined above, used in accordance with the invention, are preferably represented by the products sold by the Company Henkel under the name APG, such as the products APG 300, APG 350, APG 500, APG 550, APG 625 or APG base 10–12; the products sold by the company Seppic under the names TRITON CG 110 (or ORAMIX CG 110) and TRITON CG 312 (or ORAMIX NS 10); those sold by the Company BASF under the name LUTENSOL GD 70.

The preferred alkylpolyglycosides of formula (I), according to the invention, are APG 300 of the Company Henkel, TRITON CG 110 of the Company Seppic and LUTENSOL GD 70 of the Company BASF.

The cosmetic compositions, according to the invention, may be used in particular as shampoos or in the form of shower gels or foam baths for the body.

The cosmetic compositions in accordance with the present invention may additionally contain other surface-active agents, different from those of formula (I), chosen from anionic, amphoteric, zwitterionic or nonionic surface-active agents or mixtures thereof.

Among anionic surface-active agents, there may more particularly be mentioned the alkal metal, magnesium, ammonium, amine or aminoalcohol salts of the following compounds:

alkyl sulfates, alkyl ether sulfates, alkyl-amido ether sulfates, alkyl aryl polyether sulfates or monoglyceride sulfates;

alkyl sulfonates, alkylamide sulfonates, alkyl aryl sulfonates, olefin sulfonates or paraffin sulfonates;

alkyl sulfosuccinates, alkyl ether sulfosuccinates or alkylamide sulfosuccinates;

alkyl sulfosuccinamates;

alkyl sulfoacetates;

alkyl phosphates or alkyl ether phosphates;

acylsarcosinates, acylisethionates or N-acyltaurates, the alkyl or acyl radical of these various compounds generally consisting of a carbon chain containing from 12 to 20 carbon atoms.

Among anionic surface-active agents, there may also be mentioned:

fatty acid salts such as the salts of oleic, ricinoleic, palmitic or stearic acids; coconut oil acid or hydrogenated coconut oil acid; or acyllactylates, the acyl radical of which contains from 8 to 20 carbon atoms.

Among surface-active agents regarded as weakly anionic, there may be mentioned:

polyoxyalkylenated ether carboxylic acids, corresponding to the formula:

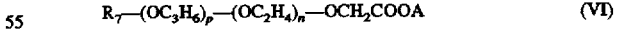

R₇—(OC₃H₆)$_p$—(OC₂H₄)$_n$—OCH₂COOA    (VI)

in which R₇ denotes a linear or branched, $C_8$-$C_{22}$ alkyl or alkenyl radical or a mixture of linear or branched, $C_8$-$C_{22}$ alkyl or alkenyl radicals, a ($C_8$-$C_9$)alkylphenyl radical or R'₇CONH—CH₂—CH₂ with R'₇ denoting a linear or branched, $C_{11}$-$C_{21}$ alkyl or alkenyl radical;

n is an integer or decimal number between 2 and 24, p is an integer or decimal number between 0 and 6, A denotes a hydrogen atom or alternatively Na, K, Li, ½ Mg or a monoethanolamine, ammonium or triethanoiamine residue.

The polyoxyethylenated ether carboxylic acids which can be used in accordance with the invention are preferably chosen from the compounds of formula (VI) in which $R_7$ denotes a ($C_{10}$–$C_{18}$)alkyl radical or a mixture of ($C_{10}$–$C_{18}$) alkyl radicals, oleoyl, or a nonylphenyl or octyl-phenyl radical. A denotes a hydrogen or sodium atom, and p is equal to 0.

The commercial products sold by the Company Chem Y under the names AKYPO or by the Company Sandoz under the names SANDOPAN are preferably used.

The nonionic surface-active agents are more particularly chosen from polyethoxylated, polypropoxylated or polyglycerolated alcohols, alkylphenols or fatty acids possessing a fatty chain containing 8 to 18 carbon atoms, the number of ethylene oxide or propylene oxide groups being between 2 and 50, and the number of glycerol groups being between 2 and 30.

There may also be mentioned copolymers of ethylene oxide and of propylene oxide, condensates of ethylene oxide and of propylene oxide with fatty alcohols, polyethoxylated fatty amides, preferably having 2 to 30 mol of ethylene oxide, polyglycerolated fatty amides containing 1 to 5, and preferably 1.5 to 4 glycerol groups, polyethoxylated fatty amines, preferably having 2 to 30 mol of ethylene oxide, oxyethylenated or nonoxyethylenated fatty acid esters of sorbitan, preferably having 2 to 30 mol of ethylene oxide, fatty acid esters of sucrose, fatty acid esters of polyethylene glycol, fatty acid esters of glycols, or amine oxides such as alkylamine oxides or N-acylamidopropylmorpholine oxide.

The more particularly preferred amphoteric or zwitterionic surface-active agents are:

derivatives of secondary or tertiary aliphatic amines, in which the aliphatic radical is a linear or branched chain containing 8 to 18 carbon atoms and which contains at least one water-solubilizing [sic] carboxyl, sulfonate, sulfate, phosphate or phosphonate anionic group;

($C_8$–$C_{20}$)alkyl betaines, sulfobetaines, ($C_8$–$C_{20}$) alkylamido($C_1$–$C_6$)alkyl betaines or ($C_8$–$C_{20}$)alkylamido ($C_1$–$C_6$)alkyl sulfobetaines.

Among the amine derivatives, there may be mentioned the products sold under the name MIRANOL, as described in U.S. Pat. Nos. 2,528,378 and 2,781,354 and classified in the CTFA dictionary, 3rd Edition, 1982, under the name of amphocarboxyglycinates and amphocarboxypropionates.

The betaines are preferably chosen from ($C_{10}$–$C_{20}$) alkylbetaines.

The amount of surface-active agents, besides alkylpolyglycoside, in these washing compositions is generally less than 20% by weight with respect to the total weight of the composition.

The compositions according to the invention have a pH generally between 2 and 9, and more particularly between 3 and 8.

The compositions, according to the invention, may also contain viscosity regulating agents, such as electrolytes such as sodium chloride or sodium xylenesulphonate, hydrotropic agents, thickening agents such as cellulose derivatives, such as for example carboxymethyl cellulose, hydroxypropyl cellulose, hydroxyethylcellulose, guar gum, hydroxypropylated guar gums, scleroglucans or xanthan gum.

These viscosity regulating agents are used in proportions ranging up to 15% by weight with respect to the total weight of the composition, and preferably less than 6%.

The compositions in accordance with the invention may additionally optionally contain other agents having the effect of improving the cosmetic properties of hair and/or of the skin, provided that they do not detrimentally affect the stability of the compositions, such as cationic surface-active agents, polymers, quaternized or nonquaternized proteins or water-soluble silicones.

Polymers, cationic surface-active agents and quaternized or nonquaternised proteins are used in the cosmetic or dermatological compositions, according to the invention, in proportions between 0.05 and 6%, and preferably between 0.1 and 3%, with respect to the total weight of the composition.

Water-soluble silicones may be used in the compositions, according to the invention, in proportions ranging up to 10%, and preferably between 0.5 and 6%, with respect to the total weight of the composition.

The compositions according to the invention may also contain various adjuvants commonly used in cosmetics, such as fragrances, preserving agents, sequestering agents, foam stabilizing agents, propellants, dyes, acidifying or basifying agents or other adjuvants depending on the use envisaged.

The dermatological compositions additionally contain an active substance for treatment of dermatological ailments.

The processes for washing and/or conditioning hair or the skin consist in applying to these a composition as defined above, this application being followed by rinsing.

The examples which follow illustrate the present invention without, however, limiting it.

| EXAMPLE 1 | |
|---|---|
| Alkylpolyglucoside [sic] sold under the name APG 300 by the Company Henkel, containing 50% of AM | 20.0 g AM |
| Compound of formula: | |
| $C_{16}H_{33}O[C_2H_3(OH)]$–R (I) with R = mixture of $C_{16}H_{33}$ and $C_{18}H_{37}$ radicals | 2.0 g |
| Coconut acid monoisopropanolamide | 1.5 g |
| Carbopol 940 (Goodrich) | 0.2 g |
| γ-hydroxypropylated polydimethylsiloxane, sold under the name of 71 615 V 300 oil by Rhône-Poulenc | 2.0 g |
| Preserving agent, fragrance qs | |
| Triethanolamide [sic] qs pH = 7.2 | |
| Water qs for | 100 g |

| EXAMPLE 2 | |
|---|---|
| APG 300 containing 50% of AM (Henkel) | 12.5 g AM |
| Ethylene glycol distearate | 1.5 g |
| Coconut acid diethanolamide | 2.0 g |
| Polyethylene glycol 6000 distearate | 3.0 g |
| Polydimethylsiloxane containing mercaptopropyl groups, sold under the name X 28360 by the Company Dow Corning | 2.5 g |
| Preserving agent, fragrance qs | |
| Hydrochloric acid qs pH = 7.5 | |
| Water qs for | 200 g |

| EXAMPLE 3 | |
|---|---|
| APG 300 containing 50% of AM (Henkel) | 15.0 g AM |
| Compound of formula (I) described in Example 1 | 1.5 g |
| Coconut acid monoisopropanolamide | 2.0 g |
| Carbopol 940 (Goodrich) | 0.3 g |
| Polydimethylsiloxane containing amide groups, sold under the name X 28491 by Dow Corning | 3.0 g |
| Preserving agent, fragrance qs | |
| Hydrochloric acid qs pH = 7 | |
| Water qs for | 200 g |

EXAMPLE 4

| | |
|---|---|
| APG 300 containing 50% of Am (Henkel) | 25.0 g AM |
| Ethylene glycol distearate | 1.0 g |
| Coconut acid monoisopropanolamide | 2.0 g |
| Polydimethylsiloxane/trimethyl-siloxysilicate mixture, sold under the name DC 593 by Dow Corning | 1.0 g |
| Fragrance, preserving agent qs | |
| Hydrochloric acid qs pH = 7.2 | |
| Water qs for | 100 g |

EXAMPLE 5

| | |
|---|---|
| APG 300 containing 50% of AM (Henkel) | 12.0 g AM |
| Polydimethylsiloxane containing stearate groups, sold under the name 71 019 Oil by Rhône-Poulenc (1) | 2.5 g |
| Polydimethylsiloxane containing amide groups (X 28491/Dow Corning) | 0.5 g |
| Polyethylene glycol 6000 distearate | 3.2 g |
| Preserving agent, fragrance qs | |
| HCl qs pH = 7 | |
| Water qs for | 100 g |

(1) polyorganosiloxane of formula:

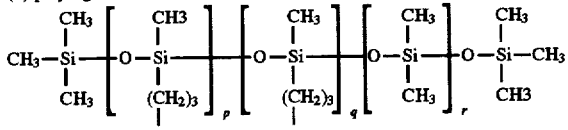

R" = mixture of $C_{16}H_{33}$ and $C_{18}H_{37}$ radicals
p = 7.9, q = 1.4, r = 9.3
This compound contains on average 2 $CH_3-\underset{O_{2/2}}{\underset{|}{Si}}-OH$ — units It may be prepared as described in Example A of U.S. Pat. No. 4,957,732.

EXAMPLE 6

| | |
|---|---|
| APG 300 containing 50% of AM (Henkel) | 10.0 g AM |
| Polydimethylsiloxane containing carboxyl groups, sold under the name FZ 23703 by Union Carbibe [sic] | 3.0 g |
| Xanthan gum sold under the name Keltrol T by Kelco | 1.2 g |
| Lauryl betaine containing 32% of AM | 5.0 g AM |
| Fragrance, preserving agent qs | |
| pH = 5.7 | |
| Water qs for | 100 g |

EXAMPLE 7

| | |
|---|---|
| Alkylpolyglycoside sold under the name Lutensol GD 70 by BASF, containing 70% of AM | 30.0 g AM |
| Polydimethylsiloxane containing thiol functional groups, sold under the name SLM 50253/5 by Wacker | 1.0 g |
| Xanthan gum (Keltrol T) | 1.8 g |
| Polyglycerolated (4 mol) lauryl alcohol | 5.0 g AM |
| Fragrance, preserving agent qs | |
| pH = 7.5 | |
| Water qs for | 100 g |

EXAMPLE 8

| | |
|---|---|
| Alkylpolyglucoside [sic] sold under the | 30.0 g AM |
| Ethylene glycol distearate | 2.0 g |
| Coconut acid monoisopropanolamide | 1.5 g |
| Polydiphenyldimethylsiloxane gum, sold under the name 761 Gum by the Company Rhône-Poulenc | 1.0 g |
| Mixture of tetramethylhexanes/heptanes octanes, sold under the name of Isopar H by the Company Exxon | 2.0 g |
| Preserving agent, fragrance qs | |
| Water qs for | 100 g |

I claim:
1. Foamable washing composition for hair or skin treatment, consisting essentially of, in an aqueous medium:
a) from 0.2 to 30% by weight relative to the total weight of the composition of a silicone which is insoluble in said medium and unreactive with said medium selected from the group consisting of:
(i) silicone gums consisting of polydiorgano-siloxanes having high molecular weight between 200,000 and 1,000,000;
(ii) organopolysiloxane resins which are cross-linked siloxane systems, containing $R'_2SiO_{2/2}$, $R'SiO_{3/2}$ and $SiO_{4/2}$ units in which R' represents a hydrocarbon group having 1 to 6 carbon atoms or a phenyl group;
(iii) polyalkylsiloxanes, polyarylsiloxanes or polyalkylarylsiloxanes containing, in their structure, one or a number of functional groups selected from the GROUP consisting of thiol, carboxylate, hydroxyalkylsulfonate, hydroxyalkylthiosulfate and hydroxyacylamino connected to the siloxane chain and connected via a hydrocarbon radical;
(iv) organomodified silicones containing γ-hydroxypropyl groups corresponding to the formula:

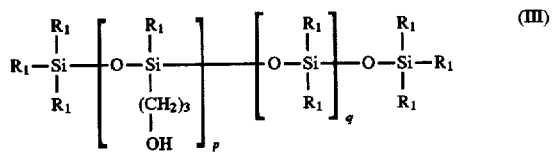

in which:
the radicals $R_1$, which are identical or different, are selected from the group consisting of methyl and phenyl radicals, at least 60 mol % of the radicals $R_1$ denoting methyl:
p is between 1 and 30 inclusive; and
q is between 1 and 150 inclusive;
(v) organomodified silicones containing acyloxy alkyl groups corresponding to the formula:

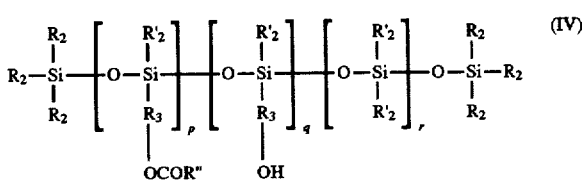

in which
$R_2$ denotes a methyl, phenyl, —OCOR" or hydroxyl group, only one of the radicals $R_2$ per silicon atom may be OH;
$R'_2$ denotes methyl or phenyl, at least 60 mol % of the radicals $R_2$ and $R'_2$ combined denoting methyl;

R" denotes a $C_8$–$C_{20}$ alkyl or alkenyl;

$R_3$ denotes a linear or branched, divalent $C_2$–$C_{18}$ alkylene hydrocarbon radical;

r is between 1 and 120 inclusive;

p is between 1 and 30;

q is equal to 0 or less than 0.5 p, p+q being between 1 and 30; it being possible for the polyorganosiloxanes of formula (IV) to contain $CH_3Si$—OH $O_{2/2}$ in proportions not exceeding 15% of the sum p+q+r; and (vi) mixtures of the organomodified silicones as defined in paragraphs (iii) to (v); and b) from 4 to 60% by weight relative to the total weight of the composition of at least one compound corresponding to the expanded structure:

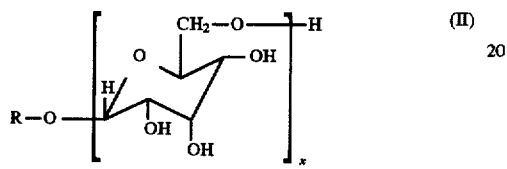

in which:

R denotes a straight- or branched-chain, $C_8$–$C_{24}$ alkyl or alkenyl radical or a mixture of straight- or branched-chain, $C_8$–$C_{24}$ alkyl or alkenyl radicals;

x is a number from 1 to 15;

the compound of formula (II)/silicone ratio by weight being greater than or equal to 1.

2. Composition according to claim 1, wherein the silicone gums are selected from the group consisting of poly(dimethylsiloxane/methylvinylsiloxane), poly(dimethylsiloxane/diphenylsiloxane), poly(dimethylsiloxane/phenylmethylsiloxane) and poly(dimethylsiloxane/diphenylsiloxane/methylvinylsiloxane) gums.

3. Composition according to claim 1, wherein the organomodified silicones containing a hydroxyacylamino functional group correspond to the formula:

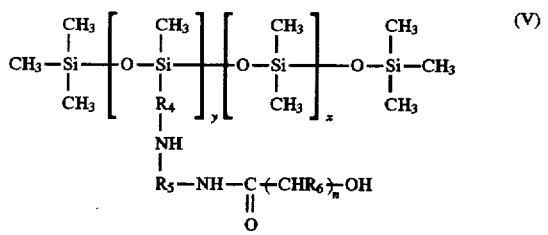

in which:

$R_4$ and $R_5$ denote $(CH_2)_2$, $(CH_2)_3$, $(CH_2)_4$ or —$CH_2CH(CH_3)CH_2$—;

$R_6$ denotes hydrogen, hydroxyl, alkyl or hydroxyalkyl;

n is an integer varying from 2 to 7;

x is an integer varying from 20 to approximately 1500;

y varies between approximately 0.5 and 10; and and the ratio y/x is less than 0.05.

4. Composition according to claim 1, wherein the silicone is present in proportions of between 0.4 and 15% by weight with respect to the total weight of the composition.

5. Composition according to claim 1, wherein the composition is in the form of a shampoo, shower gel or foam bath for the body.

6. Composition according to claim 1, wherein it additionally contains anionic, amphoteric, zwitterionic or nonionic surface-active agents, or mixtures thereof, different from those of formula (I) as defined in claim 1.

7. Composition according to claim 6, wherein the anionic surface-active agents are selected from the group consisting of alkali metal salts, magnesium salts, ammonium salts, amine salts and aminoalcohol salts of the following compounds:

alkyl sulfates, alkyl ether sulfates, alkylamido ether sulfates, alkyl aryl polyether sulfates and monoglyceride sulfates;

alkyl sulfonates, alkylamide sulfonates, alkyl aryl sulfonates, olefin sulfonates and paraffin sulfonates;

alkyl sulfosuccinates, alkyl ether sulfosuccinates and alkylamide sulfosuccinates;

alkyl sulfosuccinamates;

alkyl sulfoacetates;

alkyl phosphates and alkyl ether phosphates;

acylsarcosinates, acylisethionates and N-acyltaurates, the alkyl and acyl radical of these various compounds generally consisting of a carbon chain containing from 12 to 20 carbon atoms;

fatty acid salts; coconut oil acid and hydrogenated coconut oil acid; and acyllactylates, the acyl radical of which contains from 8 to 20 carbon atoms;

polyoxyalkylenated ether carboxylic acids, corresponding to the formula:

$$R_7\text{—}(OC_3H_6)_p\text{—}(OC_2H_4)_n\text{—}OCH_2COOA \quad (VI)$$

in which $R_7$ denotes a linear or branched, $C_8$–$C_{22}$ alkyl or alkenyl radical or a mixture of linear or branched, $C_8$–$C_{22}$ alkyl or alkenyl radicals, a ($C_8$–$C_9$)alkylphenyl radical or $R'_7CONH$—$CH_2$—$CH_2$ with $R'_7$ denoting a linear or branched, $C_{11}$–$C_{21}$ alkyl or alkenyl radical;

n is an integer or decimal number between 2 and 24, p is an integer or decimal number between 0 and 6, A denotes a hydrogen atom or Na, K, Li, ½ Mg or a monoethanolamine, ammonium or triethanolamine residue.

8. Composition according to claim 6, wherein the nonionic surface-active agent is selected from the group consisting of:

a) polyoxyethylenated, polypropoxylated and polyglycerolated alcohols, alkylphenols and fatty acids possessing a fatty chain containing 8 to 18 carbon atoms and comprising 2 to 50 ethylene oxide or propylene oxide groups or 2 to 30 glycerol groups;

b) copolymers of ethylene oxide and of propylene oxide, condensates of ethylene oxide and of propylene oxide with fatty alcohols, polyoxyethylenated fatty amides, polyglycerolated fatty amides, polyoxyethylenated fatty amines, fatty acid esters of glycols, oxyethylenated or nonoxyethylenated fatty acid esters of sorbitan, fatty acid esters of sucrose, fatty acid esters of polyethylene glycol and amine oxides.

9. Composition according to claim 6, wherein the amphoteric or zwitterionic surface-active agent is selected from the group consisting of:

a) secondary and tertiary aliphatic amines, in which the aliphatic radical in a linear or branched chain having 8 to 18 carbon atoms, and containing at least one water-soluble carboxyl, sulfonate, sulfate, phosphate or phosphonate anionic group; and b) $(C_8-C_{20})$alkyl betaines, sulfobetaines, $(C_8-C_{20})$ alkylamido$(C_1-C_6)$alkyl betaines and $(C_8-C_{20})$ alkylamido$(C_1-C_6)$alkyl sulfobetaines.

10. Composition according to claim 1, wherein the total amount of surface-active agents other than the compounds of formula (II) is less than 20% by weight with respect to the total weight of the composition.

11. Composition according to claim 1, wherein its pH is between 2 and 9.

12. Composition according to claim 1, wherein it additionally contains a viscosity regulating agent present in a concentration up to 15% by weight with respect to the total weight of the composition.

13. Composition according to claim 1, wherein it additionally contains hair or skin conditioning agents, which do not detrimentally affect the stability of the composition, selected from the group consisting of cationic surface-active agents, polymers, quaternized proteins, nonquaternized proteins and water-soluble silicones, the water-soluble silicones being present in proportions ranging up to 10% by weight with respect to the total weight of the composition.

14. Composition according to claim 1, wherein it additionally contains adjuvants selected from the group consisting of sequestering agents, fragrances, dyes, preserving agents, foam stabilizing agents, propellants, basifying agents, acidifying agents and other adjuvants commonly used in cosmetics.

15. Process for washing and conditioning hair or the skin, comprising applying a composition as defined according to claim 1 to hair or the skin, this application being followed by rinsing.

16. Composition according to claim 1, wherein it additionally contains an active substance for treatment of a dermatological conditions.

17. Composition according to claim 12, wherein the viscosity regulating agent is present in a concentration up to 6% by weight with respect to the total weight of the composition.

18. Composition according to claim 13, wherein the water-soluble silicones are present in proportions ranging between 0.5 and 6% by weight with respect to the total weight of the composition.

* * * * *